US00PP22066P2

(12) United States Plant Patent
Podaras

(10) Patent No.: US PP22,066 P2
(45) Date of Patent: Aug. 9, 2011

(54) ***BUDDLEJA* PLANT NAMED 'PODARAS #10'**

(50) Latin Name: ***Buddleja davidii*×*Buddleja alternifolia***
Varietal Denomination: Podaras #10

(75) Inventor: Peter Podaras, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/660,664

(22) Filed: Mar. 2, 2010

(51) Int. Cl.
*A01H 5/00* (2006.01)

(52) U.S. Cl. ..... Plt./242

(58) Field of Classification Search ..... Plt./424
See application file for complete search history.

*Primary Examiner* — Susan B McCormick Ewoldt
(74) *Attorney, Agent, or Firm* — C. A. Whealy

(57) ABSTRACT

A new and distinct cultivar of *Buddleja* plant named 'Podaras #10', characterized by its compact, upright and outwardly spreading plant habit; freely flowering habit; sterile dark violet-colored flowers; and good garden performance.

1 Drawing Sheet

Botanicals designation: *Buddleja davidii*×*Buddleja alternifolia.*

Cultivar denomination: 'PODARAS #10'.

BACKGROUND OF THE INVENTION

The present invention relates to a new and distinct cultivar of *Buddleja* plant, botanically known as *Buddleja davidii*× *Buddleja alternifolia* and hereinafter referred to by the name 'Podaras #10'.

The new *Buddleja* plant is a product of a planned breeding program conducted by the Inventor in Ithaca, N.Y. The objective of the breeding program was to create new compact and sterile *Buddleja* plants with unique and attractive flower coloration.

The new *Buddleja* plant originated from an open-pollination on Mar. 15, 2005 in Ithaca, N.Y., of an unnamed selection of *Buddleja davidii*×*Buddleja alternifolia,* not patented, as the female, or seed, parent with an unknown selection of *Buddleja davidii*×*Buddleja alternifolia,* not patented, as the male, or pollen, parent. The new *Buddleja* plant was discovered and selected by the Inventor as a single flowering plant within the progeny of the stated open-pollination in a controlled environment in Ithaca, N.Y. in August, 2005.

Asexual reproduction of the new *Buddleja* plant by cuttings in a controlled greenhouse environment in West Chicago, Ill. since February, 2008, has shown that the unique features of this new *Buddleja* plant are stable and reproduced true to type in successive generations.

SUMMARY OF THE INVENTION

Plants of the new *Buddleja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Podaras #10'. These characteristics in combination distinguish 'Podaras #10' as a new and distinct *Buddleja* plant:

1. Compact, upright and outwardly spreading plant habit.
2. Freely flowering habit.
3. Sterile dark violet-colored flowers.
4. Good garden performance.

Plants of the new *Buddleja* differ from plants of the female parent selection in the following characteristics:

1. Plants of the new *Buddleja* are more compact and uniform than plants of the female parent selection.
2. Plants of the new *Buddleja* and the female parent selection differ in flower color as plants of the female parent selection have pale mauve-colored flowers.

Plants of the new *Buddleja* can be compared to plants of *Buddleja davidii* 'Pink Delight', not patented. In side-by-side comparisons, plants of the new *Buddleja* and 'Pink Delight' differed in the following characteristics:

1. Plants of the new *Buddleja* were more compact and more uniform than plants of 'Pink Delight'.
2. Plants of the new *Buddleja* were more freely branching than plants of 'Pink Delight'.
3. Plants of the new *Buddleja* and 'Pink Delight' differed in leaf color as plants of 'Pink Delight' had silvery-colored leaves.

BRIEF DESCRIPTION OF THE PHOTOGRAPHS

The accompanying colored photographs illustrate the overall appearance of the new *Buddleja* plant, showing the colors as true as it is reasonably possible to obtain in colored reproductions of this type. Colors in the photographs may differ slightly from the color values cited in the detailed botanical description which accurately describe the colors of the new *Buddleja* plant.

The photograph at the bottom of the sheet comprises a side perspective view of a typical flowering plant of 'Podaras #10' grown in a container.

The photograph at the top of the sheet is a close-up view of a typical inflorescence of 'Podaras #10'.

DETAILED BOTANICAL DESCRIPTION

The aforementioned photographs and following observations, measurements and values describe plants grown in Arroyo Grande, Calif. under commercial practice during the summer in 12.5-cm containers in a polyethylene-covered greenhouse with day temperatures averaging 21° C. and night temperatures averaging 7° C. Plants were pinched two times and were three months old when the photographs and description were taken. In the following description, color references are made to The Royal Horticultural Society Colour Chart, 2007 Edition, except where general terms of ordinary dictionary significance are used.

Botanical classification: *Buddleja davidii*×*Buddleja alternifolia* 'Podaras #10'.

Parentage:

*Female, or seed, parent.*—Unnamed selection of *Buddleja davidii*×*Buddleja alternifolia,* not patented.

*Male, or pollen, parent.*—Unknown selection of *Buddleja davidii*×*Buddleja alternifolia,* not patented.

Propagation:

*Type.*—By cuttings.

*Time to initiate roots plant, summer.*—About two weeks at temperatures of 18° C. to 24° C.

*Time to initiate roots plant, winter.*—About two to three weeks at temperatures of 18° C. to 24° C.

*Time to produce a rooted plant, summer.*—About three weeks at temperatures of 18° C. to 24° C.

*Time to produce a rooted plant, winter.*—About three to four weeks at temperatures of 18° C. to 24° C.

*Root description.*—Fibrous, fine; white in color.

*Rooting habit.*—Freely branching; moderately dense.

Plant description:

*Plant form/habit.*—Deciduous perennial shrub; compact, upright and outwardly spreading plant habit; broad inverted triangle; vigorous growth habit.

*Plant height.*—About 26 cm.

*Plant width* (*spread*).—About 33 cm by 58 cm.

*Lateral branches.*—Quantity: About eight main branches per plant. Length: About 30 cm. Diameter: About 2 mm. Internode length: About 4.4 cm. Strength: Strong. Texture, developing stems: Pubescent. Texture, mature stems: Smooth, glabrous. Color, developing: Close to 146C. Color, mature: Close to N199A.

Foliage description:

*Arrangement.*—Opposite, simple.

*Length.*—About 5.2 cm.

*Width.*—About 1.5 cm.

*Shape.*—Narrowly elliptical.

*Apex.*—Acute.

*Base.*—Attenuate.

*Margin.*—Serrulate.

*Texture, upper and lower surfaces.*—Pubescent.

*Venation pattern.*—Pinnate, reticulate.

*Color.*—Developing leaves, upper surface: Close to 137B. Developing leaves, lower surface: Close to 148B. Fully expanded leaves, upper surface: Close to 137A; venation, close to 137C. Fully expanded leaves, lower surface: Close to 148B; venation, close to 148B.

*Petiole.*—Length: About 6 mm. Diameter: About 1 mm. Texture, upper and lower surfaces: Pubescent. Color, upper and lower surfaces: Close to 146C.

Flower description:

*Flower type/habit.*—Single rotate and salverform flowers arranged in compound terminal and axillary panicles; flowers face upright and outward; panicles roughly conical in shape; freely flowering habit with about 115 flower buds and flowers developing per inflorescence.

*Fragrance.*—Faint, sweet.

*Natural flowering season.*—Plants begin flowering about three months after planting; flowering continuous from spring until frost in California.

*Postproduction longevity.*—Flowers last about three to four days on the plant; flowers persistent.

*Flower buds.*—Height: About 9 mm. Diameter: About 2 mm. Shape: Oblong. Color: Close to N92B.

*Inflorescence height.*—About 9 cm.

*Inflorescence diameter.*—About 2.8 cm.

*Flower diameter.*—About 8 mm.

*Flower depth.*—About 1.2 cm.

*Flower throat, diameter.*—About 2 mm.

*Flower tube, length.*—About 9 mm.

*Flower tube, diameter at base.*—About 2 mm.

*Petals.*—Quantity per flower: Typically four in a single whorl; petals fused into a narrow tube. Lobe length: About 4 mm. Lobe width: About 3.5 mm. Lobe shape: Roughly spatulate. Lobe apex: Rounded. Lobe margin: Erosulate, crinkled. Texture, upper and lower lobe surfaces: Smooth, glabrous. Texture, throat: Slightly pubescent. Texture, tube: Slightly pubescent. Color: Developing petals, upper surface: Close to N92B. Developing petals, lower surface: Close to N92B. Fully expanded petals, upper surface: Close to 86A; towards the margins, close to 93A; venation, close to 86A; color becoming closer to 86D with development. Fully expanded petals, lower surface: Close to 86B; venation, close to 86B. Throat: Close to 174A; venation, close to 174A. Tube: Close to 79B; venation, close to 79B.

*Sepals.*—Quantity per flower: Typically four in a single whorl, fused towards the base; campanulate calyx. Length: About 2 mm. Width: About 1 mm. Shape: Lanceolate. Apex: Acute. Margin: Entire. Texture, upper surface: Smooth, glabrous. Texture, lower surface: Lanulose. Color, upper surface: Close to 144B. Color, lower surface: Close to 194B; towards the apex, close to N92A.

*Peduncles*—Length: About 2.5 cm. Diameter: About 1 mm. Angle: Mostly erect. Strength: Strong. Texture: Pubescent. Color: Close to 148A.

*Pedicels.*—Length: About 3 mm. Diameter: About 1 mm. Angle: About 45° from peduncle axis. Strength: Strong. Texture: Pubescent. Color: Close to 148A.

*Reproductive organs.*—Stamens: Quantity per flower: Typically four; filaments adnate to the corolla tube. Filament length: About 2 mm. Filament color: Close to 174B. Anther shape: Lanceolate. Anther length: About 1 mm. Anther color: Close to 155A. Pollen amount: None. Pistils: Quantity per flower: One. Pistil length: About 4 mm. Stigma shape: Oval. Stigma color: Close to 145A. Style length: About 1.5 mm. Style color: Close to 79D. Ovary color: Close to 148C.

*Seed/fruit.*—Flowers of plants of the new *Buddleja* are sterile and seed and fruit development have not been observed.

Disease/pest resistance: Plants of the new *Buddleja* have been not been observed to be resistant to pathogens and pests common to *Buddleja.*

Garden performance: Plants of the new *Buddleja* have been observed to have good garden performance and tolerate rain, wind and temperatures ranging from about 0° C. to about 40° C.

It is claimed:

1. A new and distinct *Buddleja* plant named 'Podaras #10' as illustrated and described.

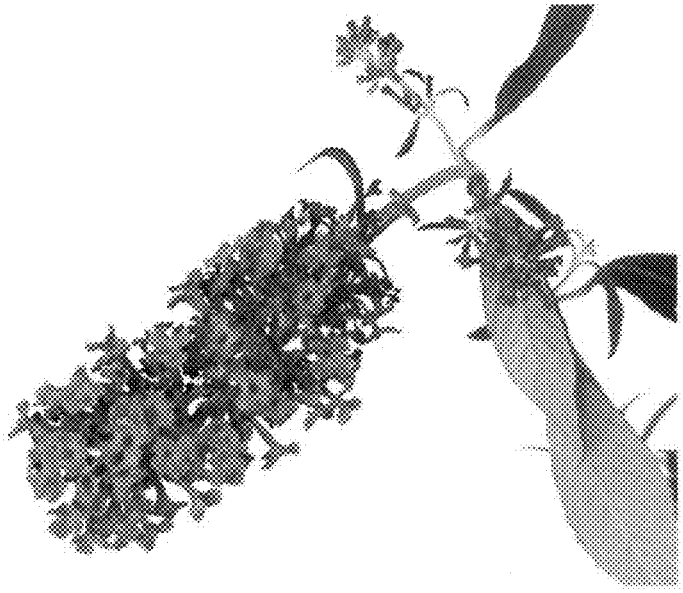
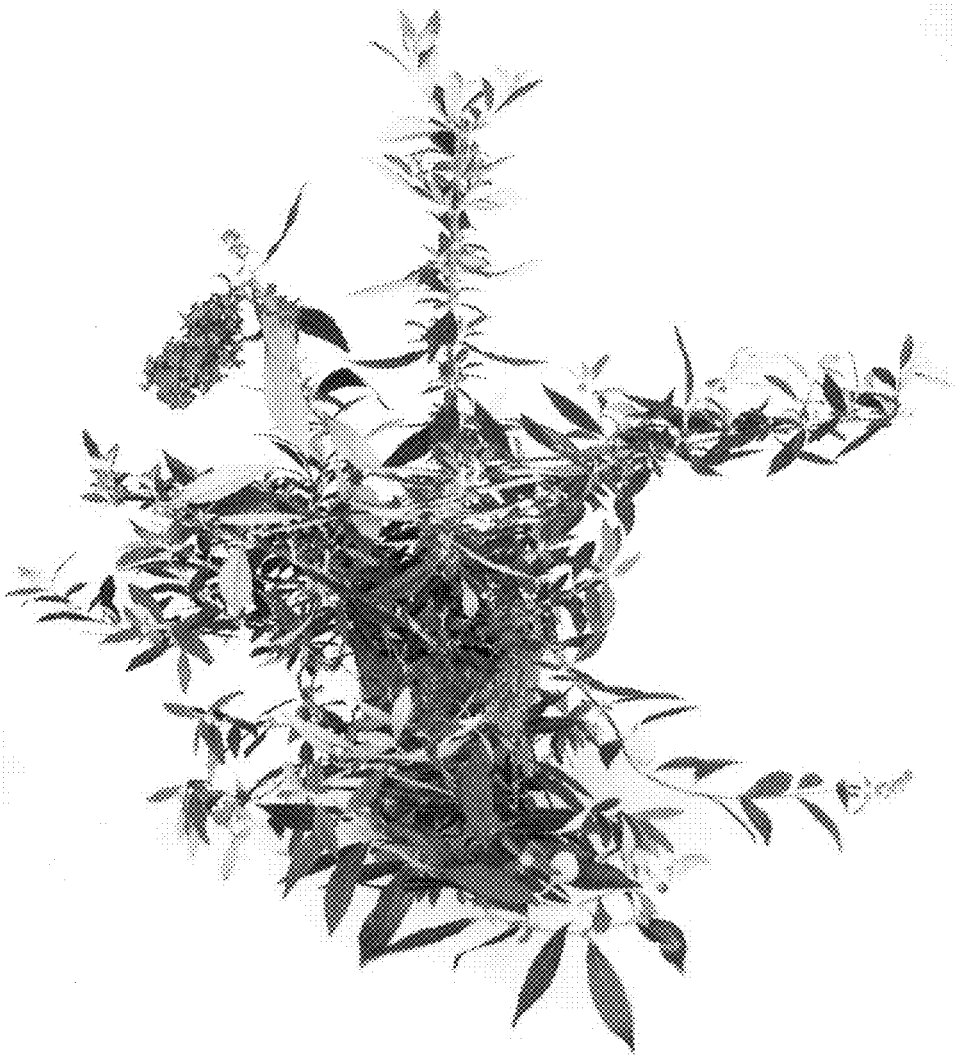

* * * * *